United States Patent [19]

Yahata et al.

[11] Patent Number: 5,436,127
[45] Date of Patent: Jul. 25, 1995

[54] EPITOPE-RELATED PEPTIDES OF HUMAN PARVOVIRUS

[75] Inventors: Ken Yahata; Yasuyoshi Koumoto; Tohru Chiba, all of Kanagawa; Tadasu Nunoue, Fukuoka, all of Japan

[73] Assignee: Shin-Etsu Chemical Co., Ltd., Tokyo, Japan

[21] Appl. No.: 139,711

[22] Filed: Oct. 21, 1993

[30] Foreign Application Priority Data

Oct. 28, 1992 [JP] Japan .................... 4-290102

[51] Int. Cl.$^6$ .................. C07K 17/00; C12Q 1/68
[52] U.S. Cl. ........................ 435/5; 530/326; 530/826
[58] Field of Search ........... 530/324, 325, 326, 826; 424/233.1

[56] References Cited

FOREIGN PATENT DOCUMENTS 9112269  8/1991  European Pat. Off. .
3939470  6/1991  Germany .

OTHER PUBLICATIONS

Scand. J. Infect. Dis. 21: 597–603, 1989, Fridell, et al "A New Peptide of Human Parvovirus B19 Antibody Detection".
Journal of Virology, Apr. 1991, pp. 1667–1672, Sato et al, "Identification Of The Region Including The Epitope For A Monoclonal Antibody Which Can Neutralize Human Parvovirus B19".
Journal of Clinical Microbiology, Jul. 1991, pp. 1376–1381, Fridell et al. "Evaluation Of A Synthetic–Peptide Enzyme-Linked Immunosorbent Assay For Immunoglobulin M To Human Parvovirus B19".
Journal of Immunological Methods, 138, (1991), pp. 125–128, Fridell et al, "A Cyclized Peptide For Studies Of Human Parvovirus B19 Infection".
Journal of Virology, Oct. 1991, pp. 5485–5490, Sato et al., "Identification And Mapping Of Neutralizing Epitopes Of Human Parvovirus B 19 By Using Human Antibodies".
Vac Regenmu-tel MHV, FEMS Microbiology Letters 100:483–487, 1992.
Virology, vol. 157, 1987, New York, pp. 534–538.
Journal of Virology, vol. 58, 1986, Washington, pp. 921–936.

*Primary Examiner*—Christine M. Nucker
*Assistant Examiner*—Julie Krsek-Staples
*Attorney, Agent, or Firm*—McAulay Fisher Nissen Goldberg & Kiel

[57] ABSTRACT

A peptide having an amino acid sequence represented by the following formula: Ser-Thr-Lys-Glu-Gly-Asp-Ser-Ser-Asn-Thr-Gly-Ala-Gly-Lys-Ala-Leu-Thr-Gly-Leu-Ser-Thr-Gly specifically reacts with antibodies against human parvovirus B19. Therefore, this peptide can be used in agents for detecting antibodies against human parvovirus B19 and in methods for detecting antibodies against human parvovirus B19.

2 Claims, 4 Drawing Sheets

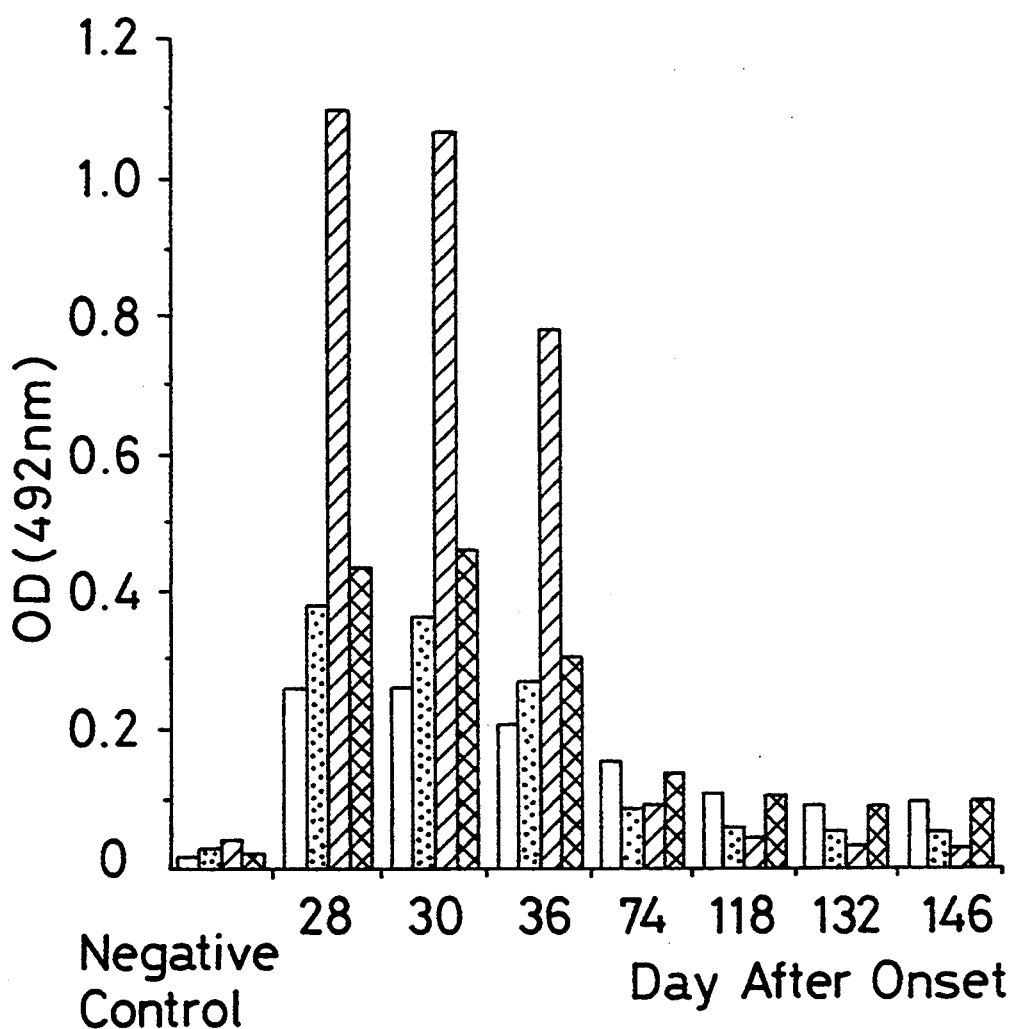

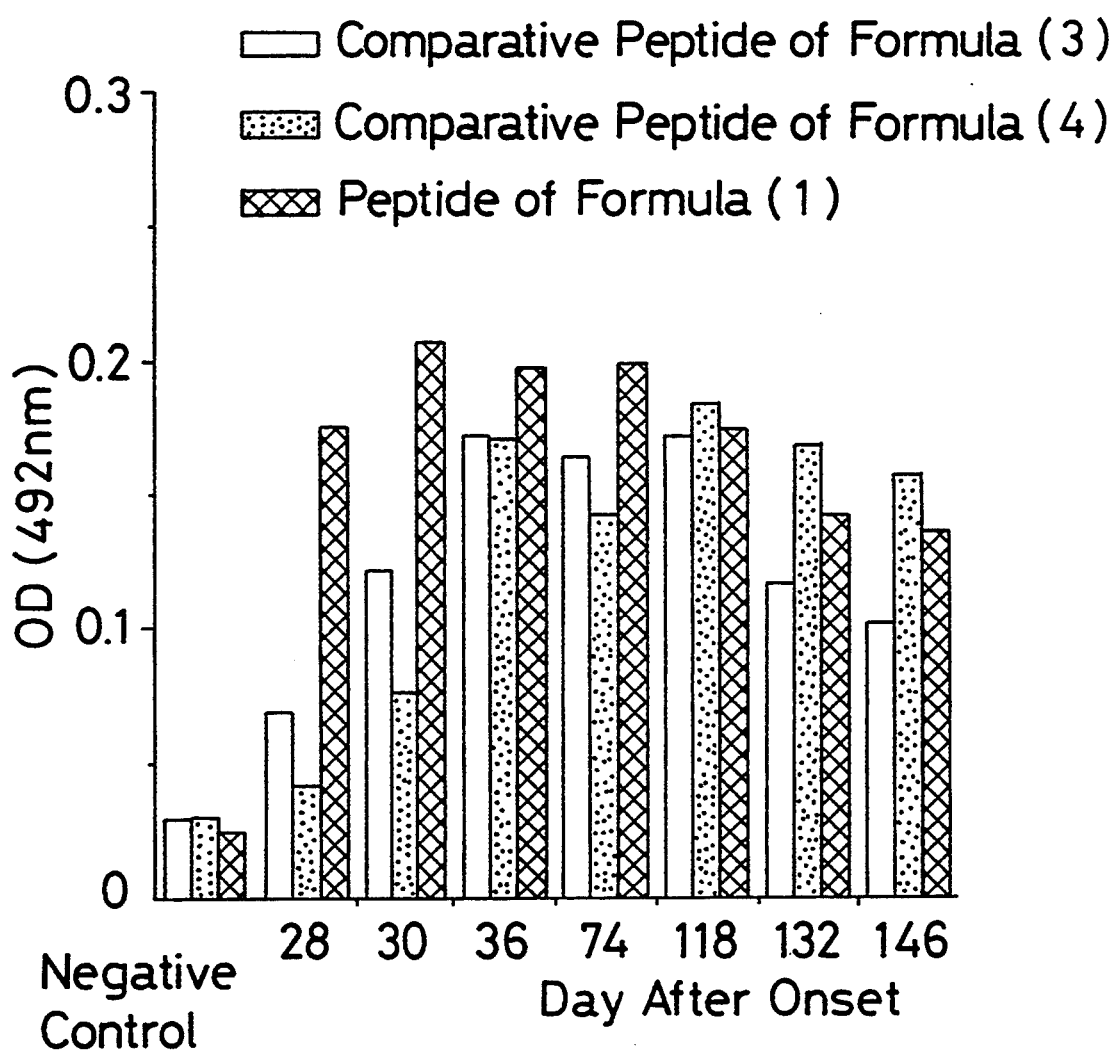

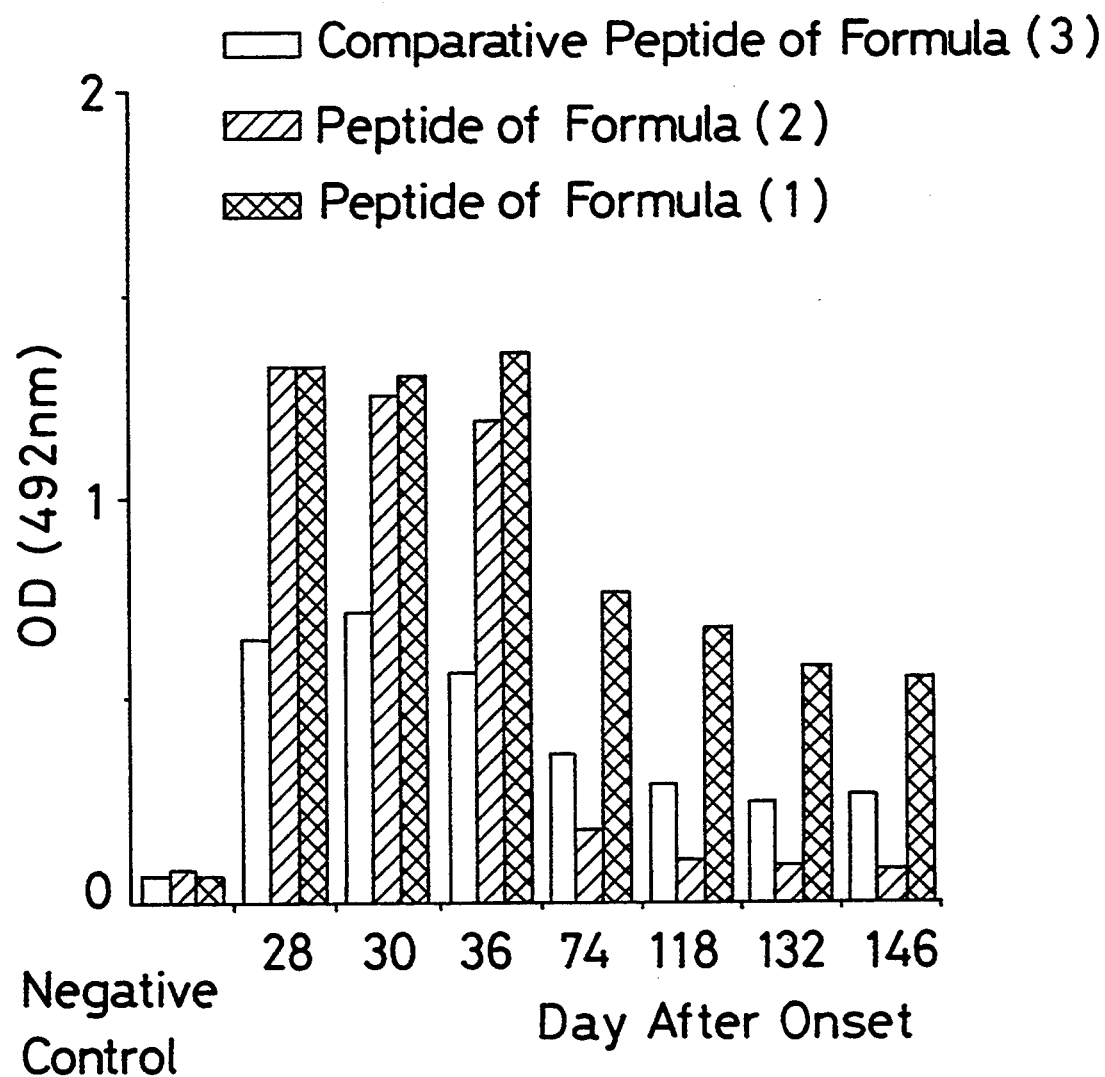

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 25 amino acids
        ( B ) TYPE: amino acid
        ( D ) TOPOLOGY: unknown ( i i ) MOLECULE TYPE: peptide ( i i i ) HYPOTHETICAL: NO ( i v ) ANTI-SENSE: NO ( v ) FRAGMENT TYPE: C-terminal ( x i ) SEQUENCE DESCRIPTION: SEQ ID NO:1:

```
Ile His Asp Phe Arg Tyr Ser Gln Leu Ala Lys Leu Gly Ile Asn Pro
 1           5                  10                  15
Tyr Thr His Trp Thr Val Ala Asp Glu
            20                  25
```

( 2 ) INFORMATION FOR SEQ ID NO:2:

( i ) SEQUENCE CHARACTERISTICS:
        ( A ) LENGTH: 22 amino acids
        ( B ) TYPE: amino acid
        ( D ) TOPOLOGY: unknown ( i i ) MOLECULE TYPE: peptide ( i i i ) HYPOTHETICAL: NO ( i v ) ANTI-SENSE: NO ( v ) FRAGMENT TYPE: C-terminal ( x i ) SEQUENCE DESCRIPTION: SEQ ID NO:2:

```
Ser Thr Lys Glu Gly Asp Ser Ser Asn Thr Gly Ala Gly Lys Ala Leu
 1           5                  10                  15
Thr Gly Leu Ser Thr Gly
            20
```

EPITOPE-RELATED PEPTIDES OF HUMAN PARVOVIRUS

BACKGROUND OF THE INVENTION

The present invention relates to epitope peptides useful in the specific detection of antibodies against human parvovirus (HPV) B19, an agent for detecting the antibody against human parvovirus B19 which comprises the epitope peptide and a method for detecting the antibody against human parvovirus B19.

Cossart et al. reported that human parvovirus B19 was detected in the human blood (Lancet, 1975, 1, pp. 72–73) and it has been revealed since 1981 that human parvovirus B19 is involved in various human diseases. Human parvovirus B19 is a causal virus of diseases such as erythema infectiosum and arthritis and it has been known that if a pregnant woman is infected with this virus, she suffers from serious diseases such as abortion and hydrops fetalis. For this reason, there has been required for precise and accurate diagnosis of patients. As such diagnostic methods, there have been known, for instance, those which comprise detection of the virus and those which comprise detection of the antibody against the virus. It is inevitable to use a substance serving as an antigen in both of these methods and this is an essential requirement for these diagnostic methods. As such antigens, there have conventionally been used, for instance, human parvovirus B19 derived from human erythroblast cells and a viral antigenic protein prepared according to a genetic engineering technique.

However, antigens derived from human are not easily available and the preparation of such antigenic substances through gene engineering techniques requires the use of complicated operations. Under such circumstances, there has been desired for the development of antigens whose stable supply can be ensured.

In general, it has been believed that an antibody recognizes several amino acid residues of the corresponding antigen and the recognized site of the antigen is called epitope. An antigenic protein has several kinds of epitopes and, therefore, the use of peptides containing these sites permits easy and specific determination or detection of the corresponding antibody without using the virus particles.

The recent progress in the solid phase synthetic technique has permitted relatively easy preparation of various peptides. The sequence of the genomic DNA (gene sequence) of the human parvovirus B19 shown in FIG. 1 was elucidated by Shade et al. (J. Virol., 1986, 58, pp. 921–936). Fridell et al. synthesized peptides corresponding to parts of open reading frame (ORF) 1 and 2 regions on the basis of the foregoing sequence of the genomic DNA and found the reactivity, with the anti-human parvovirus B19 antibody, of peptides having amino acid sequences each corresponding to the sequence extending from 236th amino acid residue to 253th amino acid residue; 284th amino acid residue to 307th amino acid residue and 732th amino acid residue to 741th amino acid residue in the ORF 1 region and the sequence extending from 161th amino acid residue to 170th amino acid residue in the ORF 2 region (Scand. J. Infect. Dis., 1989, 21, pp. 591–603). Moreover, Sato et al. suggested that the peptide having an amino acid sequence corresponding to the sequence extending from 328th amino acid residue to 344th amino acid residue in the viral protein (VP) 2 region can react with the anti-human parvovirus B19 antibody (J. Virol., 1991, 65, pp. 1667–1672).

SUMMARY OF THE INVENTION

It is, accordingly, an object of the present invention to provide peptides specific to antibodies against human parvovirus B19, applications of the peptides, i.e., agents for determining or detecting the antibodies against human parvovirus B19 and a method for determining or detecting the antibodies against human parvovirus B19.

The inventors of this invention have conducted various studies and investigations of the anti-human parvovirus B19 antibodies; and as a result, have found out the peptides which have much higher reactivity to the anti-human parvovirus B19 antibodies than those of the peptides corresponding to the foregoing sites.

A peptide specific to the anti-human parvovirus B19 antibodies comprises a part or whole of the amino acid sequence represented by the following formula (1):

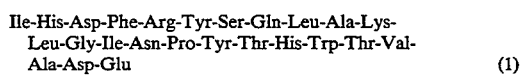

Ile-His-Asp-Phe-Arg-Tyr-Ser-Gln-Leu-Ala-Lys-
Leu-Gly-Ile-Asn-Pro-Tyr-Thr-His-Trp-Thr-Val-
Ala-Asp-Glu       (1)

The amino acid sequence represented by the foregoing formula (1) corresponds to the amino acid sequence of the peptide corresponding to that of the site of ORF 1 region extending from 152th amino acid residue to 176th amino acid residue (see FIG. 1).

Another peptide specific to the anti-human parvovirus B19 antibodies comprises a part or whole of the amino acid sequence represented by the following formula (2):

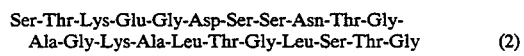

Ser-Thr-Lys-Glu-Gly-Asp-Ser-Ser-Asn-Thr-Gly-
Ala-Gly-Lys-Ala-Leu-Thr-Gly-Leu-Ser-Thr-Gly       (2)

The amino acid sequence represented by the foregoing formula (2) corresponds to the amino acid sequence of the peptide corresponding to that of the site of ORF 1 region extending from 525th amino acid residue to 546th amino acid residue (see FIG. 1).

These epitope peptides are specific to the anti-human parvovirus B19 antibodies. Moreover, the peptide represented by the formula (1) exhibits strong response to the antibody in the convalescent stage of a patient, while the peptide represented by the formula (2) exhibits strong response to the antibody in the acute stage of a patient. Therefore, a diagnostic method adapted for each stage after the infection or outbreak of a disease can be developed if these peptides represented by the formulas (1) and (2) are properly selected depending on the purposes.

BRIEF DESCRIPTION OF THE DRAWINGS

FIG. 2 is a diagram showing the results of IgG measurements;

FIG. 3 is a diagram showing the results of IgM measurements; and

FIG. 4 is a diagram showing the results of IgG measurements which make use of the biotin-avidin affinity.

DETAILED EXPLANATION OF THE INVENTION

Figure 1:
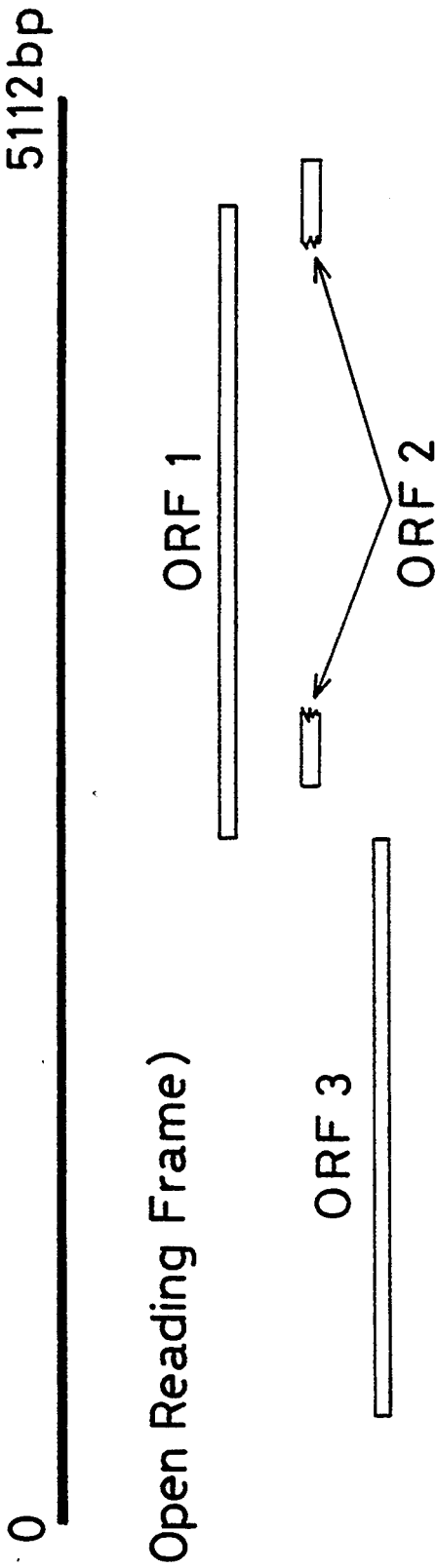
FIG. 1 is a diagram illustrating the correspondence of the gene sequence of the human parvovirus B19 and the open reading frame; and that of the human parvovirus RNA and the protein.
Figure 1:
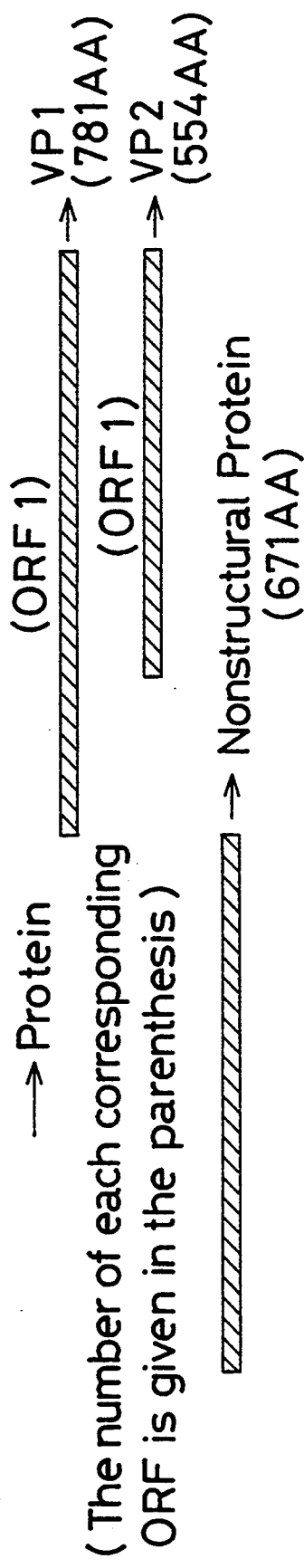

The peptides of the present invention are specific to the anti-human parvovirus B19 antibodies. For this reason, the peptides of the present invention can be used as agents for determining or detecting the anti-human parvovirus B19 antibodies. Moreover, the use of these agents for detection permits highly sensitive and specific detection of the anti-human parvovirus B19 antibodies present in the serum or plasma collected from a patient infected with this virus. Furthermore, the peptides of the present invention may be used as vaccines for stimulating immunity against various diseases such as erythema infectiosum and arthritis due to infection with human parvovirus B19 and the antibodies obtained through the use of these peptides may be used as therapeutic agents for treating these diseases due to infection with human parvovirus B19.

These peptides can be prepared through decomposition of proteins with enzymes or chemical synthetic methods, but the latter is preferably used since they are simple and permit mass-production of desired peptide products. The chemical synthetic method may be either liquid phase synthetic method or solid phase synthetic method and the solid phase synthetic method may be either t-butoxycarbonyl (Boc) method or 9-fluorenyl-methoxycarbonyl (Fmoc) method. The solid phase synthetic method can be carried out in automatic synthesizer. The functional groups of the peptides prepared through these chemical methods are protected and therefore, the protective groups should be removed from the protected peptides. More specifically, the protective groups thereof may be removed according to any currently known methods such as hydrogen fluoride methods, catalytic reduction methods, trifluoroacetic acid methods, trimethylsilyl bromide (TMSBr) methods and trimethylsilyl trifluoromethanesulfonate (TMSOTf) methods to give desired peptides free of protective groups. It is desirable to ultimately purify the peptides thus prepared through reverse phase liquid chromatography and/or gel filtration techniques.

The peptides represented by the formulas (1) and (2) exhibit high affinities specific to the anti-human parvovirus B19 antibodies and accordingly, can be used as highly sensitive and specific agents for detecting the anti-human parvovirus B19 antibodies.

Moreover, any known immunological methods may be used as means for detecting the anti-human parvovirus B19 antibodies which make use of the peptides represented by the formulas (1) and (2). Specific examples of such detection methods include the radioimmunoassay (RIA), the enzyme-linked immunosorbent assay (ELISA), the immunofluorescent technique, the chemiluminescent immunological technique and the immunoagglutination technique.

These detection systems each comprises the immobilized solid support, the sample to be assayed and the labeled anti-body or a labeled antigen. The term "immobilized solid support" herein means the solid support such as glass material, plastic or polymeric substance, bound with the substance, having an ability of binding with the sample to be assayed. The solid support may have various shapes such as a test tube, a microplate, a cuvette, beads, fine particles and a membrane. The "substance having an ability of binding with the sample to be assayed" herein means the substance having an ability of binding with antibodies, such as the antigen or against the sample to be examined, antibodies protein A. The solid support may be bound with the foregoing substance by, for instance, physical adsorption and covalently bonding method. The solid support may be bound with the substance having an ability of binding with the sample to be assayed, through substances having any available affinities such as antibody-anti-antibody affinity, biotin-avidin affinity and protein A-antibody and protein G-antibody affinities. The immobilized solid support have remaining sites for protein binding, which remain on the surface of the solid support and which take part in non-specific absorption and accordingly, it must be saturated with a blocking agent. The term "blocking agent" herein used means a substance which does not take part in the specific reaction in the detection system and examples thereof include protein components such as bovine serum albumin, ovalbumin, milk components and decomposition products of proteins; and natural and synthetic polymeric materials such as gelatin and polyvinyl alcohol. The samples to be assayed may be any substances so far as they comprise antibodies, such as serum and plasma collected from a patient infected with human parvovirus B19. Labeling materials for preparing the labeled antibodies and labeled antigens as essential components of the detection system are, for instance, radioactive materials, enzymes, fluorescent substances and chemiluminescent substances. An antibody or antigen may be labeled with the labeling material through the foregoing substance having an affinity. It is also possible to form linkage of the sample to be assayed with the labeled antibody or labeled antigen through a substance having an affinity. The peptides of the present invention can be used as the immobilized solid support or the labeled antigens among the foregoing components of the detection system.

Preparation of the peptides according to the present invention and the reactivity of the peptides with the anti-human parvovirus B19 antibodies will hereinafter be explained in more detail with reference to the following Examples.

Peptide Preparation Example

The peptides were synthesized according to the solid phase synthetic method. More specifically, each protected peptide was prepared by the Fmoc solid phase synthetic method in 430A Synthesizer available from Applied Biosystems Co., Ltd. The protective groups of each protected peptide thus prepared were removed according to the TMSOTf method to give each corresponding crude peptide. The crude peptides each was purified by, in order, gel filtration and reverse phase liquid chromatography techniques to give finally purified peptides represented by the following formulas (1) and (2):

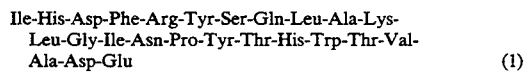
(1)

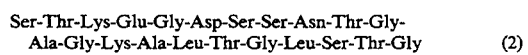
(2)

By way of comparison, peptides represented by the following formulas (3) (corresponding to the peptide reported by Fridell et al.) and (4) (corresponding to the peptide reported by Sato et al.) were also prepared in the same manner used above and used as comparative peptides:

Phe-Ser-Pro-Ala-Ala-Ser-Ser-Cys-His-Asn-Ala-Ser-
Gly-Lys-Glu-Ala-Lys-Val-Cys-Thr-Ile-Ser-Pro-
Ile         (3)

Leu-Arg-Pro-Gly-Pro-Val
-Ser-Gln-Pro-Tyr-His-His-Trp-Asp-Thr-Asp-Lys     (4)

Detection Example 1

Detection of Immunoglobulin G (IgG)

In this Detection Example, there was provided an example of the ELISA method for determining IgG antibody present in the serum collected from a patient infected with human parvovirus B19. A microplate of polystyrene was used as a solid support. A 10 μg/ml solution of peptides in phosphate-buffered saline (PBS) was distributed to wells of the microplate in an amount of 100 μl each and the microplate was allowed to stand overnight at room temperature to immobilize the peptide and to thus give an immobilized solid support. The immobilized solid support was coated with blocking agent in order to inhibit the occurrence of any non-specific adsorption due to the presence of sites free of binding with the peptide. Then the serum collected from the virus-infected patient was diluted 200 times with a commercially available diluent and distributed to the wells of the microplate provided thereon with the immobilized solid support in an amount of 100 μl each and the reaction was performed at 37° C. for 2 hours. The serum used was collected from a 12-year-old female child who had an aplastic crisis due to infection with human parvovirus B19. After washing 6 times with phosphate-buffered saline commercially available, horse radish peroxidase (HRP)-labeled anti-human IgG antibody was diluted 1000 times with phosphate-buffered saline, distributed to the wells of the microplate in an amount of 100 μl each and the reaction was continued at 37° C. for one hour. After additionally washing 6 times with phosphatebuffered saline, o-phenylenediamine (OPD: OPD 4 mg/10 ml $H_2O$, $H_2O_2$ 15 μl; 100 μl each) as a staining agent was distributed onto the microplate and the reaction was continued at room temperature for 30 minutes, the reaction was terminated by through addition of 100 μl each of a 1N—$H_2SO_4$ solution. The absorbance of the colored product at 492 nm was determined using a microplate reader to detect the activity of HRP.

The peptides used in the foregoing assay were those represented by the formulas (1) and (2). The peptides represented by the formulas (3) and (4) were also used by way of comparison. The results are plotted on the graph shown in FIG. 2. In FIG. 2, the time (day) after onset of illness is plotted as abscissa, while the absorbance is plotted as ordinate. The results shown in FIG. 2 clearly indicate that the peptides represented by the formulas (1) and (2) have high reactivity with the anti-human parvovirus B19 antibody. In addition, it is also found that the peptide represented by the formula (2) exhibited strong response to the anti-human parvovirus B19 antibodies in the acute stage of the patient.

Detection Example 2

Detection of Immunoglobulin M (IgM)

In this Detection Example, there was provided an example of the ELISA method for detecting IgM antibodies present in the serum collected from a patient infected with human parvovirus B19. Immobilized solid support were prepared and the ELISA assay was performed in the same manner used in Detection Example 1 except that an HRP-labeled anti-human IgM antibody was substituted for the HRP-labeled anti-human IgG antibody used in Example 1.

The peptide represented by the formula (1) was used in this Detection Example. The peptides represented by the formulas (3) and (4) were also used by way of comparison. The results are plotted on the graph shown in FIG. 3. The results thus obtained suggest that the peptide represented by the formula (1) also had high reactivity with IgM among the anti-human parvovirus B19 antibodies.

Detection Example 3

Detection of Immunoglobulin G (IgG) While Making Use of Biotin-Avidin Affinity

This Detection Example relates to a method for detecting IgG in which the immobilized solid support was prepared by immobilizing peptide to the solid support while making use of biotin-avidin affinity to detect IgG. More specifically, a 250 μg/ml solution of biotin-N-hydroxysuccinimide ester (NHS-Biotin) was distributed (100 μl each) in wells of a polystyrene microplate having amino groups on the surface thereof and the reaction was continued at 37° C. for 2 hours. Then the microplate was washed 6 times with phosphate-buffered saline, followed by distribution of 100 μl each of a 50 μg/ml solution of avidin to the wells of the microplate and reaction at 37° C. for one hour. Moreover, the microplate was washed 6 times with phosphate-buffered saline, followed by distribution of 100 μl each of a 50 μg/ml solution of a biotinylated peptide to the wells of the microplate and reaction at 37° C. for one hour. The biotinylated peptide herein used was prepared by coupling NHS-Biotin with the N-terminal of the protected peptide prepared according to the procedures described in the foregoing Peptide Preparation Example and then removing the protective groups and purifying the resulting crude biotinylated peptide according to the same manner used in the Peptide Preparation Example. The microplate was washed 6 times with phosphate-buffered saline, followed by blocking of the sites free of the linkages and practice of the assay.

The peptides used in the foregoing assay were those represented by the formulas (1) and (2). The peptide represented by the formula (3) was also used by way of comparison. The measured results are plotted on the graph shown in FIG. 4. The results shown in FIG. 4 clearly indicate that both of these peptides represented by the formulas (1) and (2) had high reactivity with the anti-human parvovirus B19 antibodies. In addition, it is also found that the peptide represented by the formula (1) exhibited strong response thereto in particular in the convalescent stage of the patient and that the peptide represented by the formula (2) exhibited strong response thereto in particular in the acute stage of the patient.

In this specification, amino acids are expressed in terms of the following symbols according to the recommendation issued by the committee of biochemical nomenclature in IUPAC and IUB. Moreover, the amino acids herein mean L-type ones unless otherwise specified.

| alanine | Ala | leucine | Leu |
|---|---|---|---|
| arginine | Arg | lysine | Lys |
| asparagine | Asn | methionine | Met |

| -continued | | | |
|---|---|---|---|
| aspartic acid | Asp | phenylalanine | Phe |
| cysteine | Cys | proline | Pro |
| glutamine | Gln | serine | Ser |
| glutamic acid | Glu | threonine | Thr |
| glycine | Gly | tryptophan | Trp |
| histidine | His | tyrosine | Tyr |
| isoleucine | Ile | valine | Val |

Ser-Thr-Lys-Glu-Gly-Asp-Ser-Ser-Asn-Thr-Gly-
Ala-Gly-Lys-Ala-Leu-Thr-Gly-Leu-Ser-Thr-Gly.

2. A composition for detecting antibodies against human parvovirus B19 comprising a peptide having the amino acid sequence represented by the following formula:

What is claimed is:

1. A peptide reactive with an antibody against human parvovirus B19 and having an amino acid sequence represented by the following formula:

Ser-Thr-Lys-Glu-Gly-Asp-Ser-Ser-Asn-Thr-Gly-
Ala-Gly-Lys-Ala-Leu-Thr-Gly-Leu-Ser-Thr-Gly and a support therefor.

* * * * *